(12) United States Patent
Feldmann et al.

(10) Patent No.: US 11,286,476 B2
(45) Date of Patent: Mar. 29, 2022

(54) METHODS OF PRESERVING THE BIOLOGICAL ACTIVITY OF RIBONUCLEIC ACIDS

(71) Applicants: SYNGENTA PARTICIPATIONS AG, Basel (CH); Devgen NV, Ghent (BE)

(72) Inventors: Pascale Feldmann, Ghent (BE); Jeffrey David Fowler, Greensboro, NC (US); Nema Devi Jhurry, Greensboro, NC (US); Isabelle Maillet, Ghent (BE); Marta Omedes Pujol, Berkshire (GB)

(73) Assignees: SYNGENTA PARTICIPATIONS AG, Basel (CH); Devgen NV, Ghent (BE)

( * ) Notice: Subject to any disclaimer, the term of this patent is extended or adjusted under 35 U.S.C. 154(b) by 0 days.

(21) Appl. No.: 16/339,866

(22) PCT Filed: Sep. 28, 2017

(86) PCT No.: PCT/EP2017/074697
§ 371 (c)(1),
(2) Date: Apr. 5, 2019

(87) PCT Pub. No.: WO2018/065303
PCT Pub. Date: Apr. 12, 2018

(65) Prior Publication Data
US 2020/0045977 A1 Feb. 13, 2020

Related U.S. Application Data

(60) Provisional application No. 62/404,249, filed on Oct. 5, 2016.

(51) Int. Cl.
| | | |
|---|---|---|
| C12N 15/11 | (2006.01) | |
| C12N 15/10 | (2006.01) | |
| A01N 63/60 | (2020.01) | |

(52) U.S. Cl.
CPC ......... *C12N 15/1003* (2013.01); *A01N 63/60* (2020.01); *C12N 15/111* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 2006/0172930 A1 | 8/2006 | Akiyama et al. | |
| 2007/0269892 A1* | 11/2007 | Adami | C12N 15/111 |
| | | | 435/455 |
| 2009/0285784 A1* | 11/2009 | Raemaekers | C12N 15/8286 |
| | | | 424/93.2 |
| 2010/0257634 A1 | 10/2010 | Bailey et al. | |
| 2015/0184160 A1* | 7/2015 | Brown | C12N 9/0006 |
| | | | 514/44 A |
| 2015/0337306 A1* | 11/2015 | Lieberman | A61K 31/713 |
| | | | 514/44 A |
| 2018/0289015 A1* | 10/2018 | Feldmann | C12N 15/113 |

FOREIGN PATENT DOCUMENTS

| | | |
|---|---|---|
| CN | 104673781 A | 6/2015 |
| EP | 2 175 020 A1 | 4/2010 |
| EP | 2 402 441 A1 | 1/2012 |
| JP | 2007308461 A | 11/2007 |
| JP | 2009523018 A | 6/2009 |
| WO | 2004069869 A1 | 8/2004 |
| WO | WO-2017060122 A1 * | 4/2017 ........... C12N 15/111 |

OTHER PUBLICATIONS

Glauert et al. Journal of the Royal Microscopical Society vol. 85 449-453 (Year: 1966).*
Lybecker et al. PNAS 111, pp. 3134-3139 (Year: 2014).*
James A. Baum; "Control of Coleopteran Insect Pests Through RNA Interference"; Nature Biotechnology, Gale Group Inc.; vol. 25, No. 11; Nov. 1, 2007; pp. 1322-1326.
T. J. Munton et al.; "Interaction of Glutaraldehyde with Spheroplasts of *Escherichia Coli*"; Journal of Applied Bacteriology; Jun. 1, 1973; pp. 211-217.

* cited by examiner

*Primary Examiner* — Brian Whiteman
(74) *Attorney, Agent, or Firm* — BakerHostetler; Toni-Junell Herbert

(57) ABSTRACT

Methods of substantially retaining or otherwise preserving the biological activity of a dsRNA, present in a cell, to post-transcriptionally silence the expression of a gene in a target organism, comprising the step of adding to the cell composition a compound having the function of a protein— or amine—cross linking agent and/or an acid, and compositions comprising the cells comprising dsRNA, and protein cross linking agents and/or acids, as well as the use of the cross linking agents and/or acids in the method.

12 Claims, 5 Drawing Sheets

METHODS OF PRESERVING THE BIOLOGICAL ACTIVITY OF RIBONUCLEIC ACIDS

CROSS-REFERENCE TO RELATED APPLICATIONS

Figure 1:
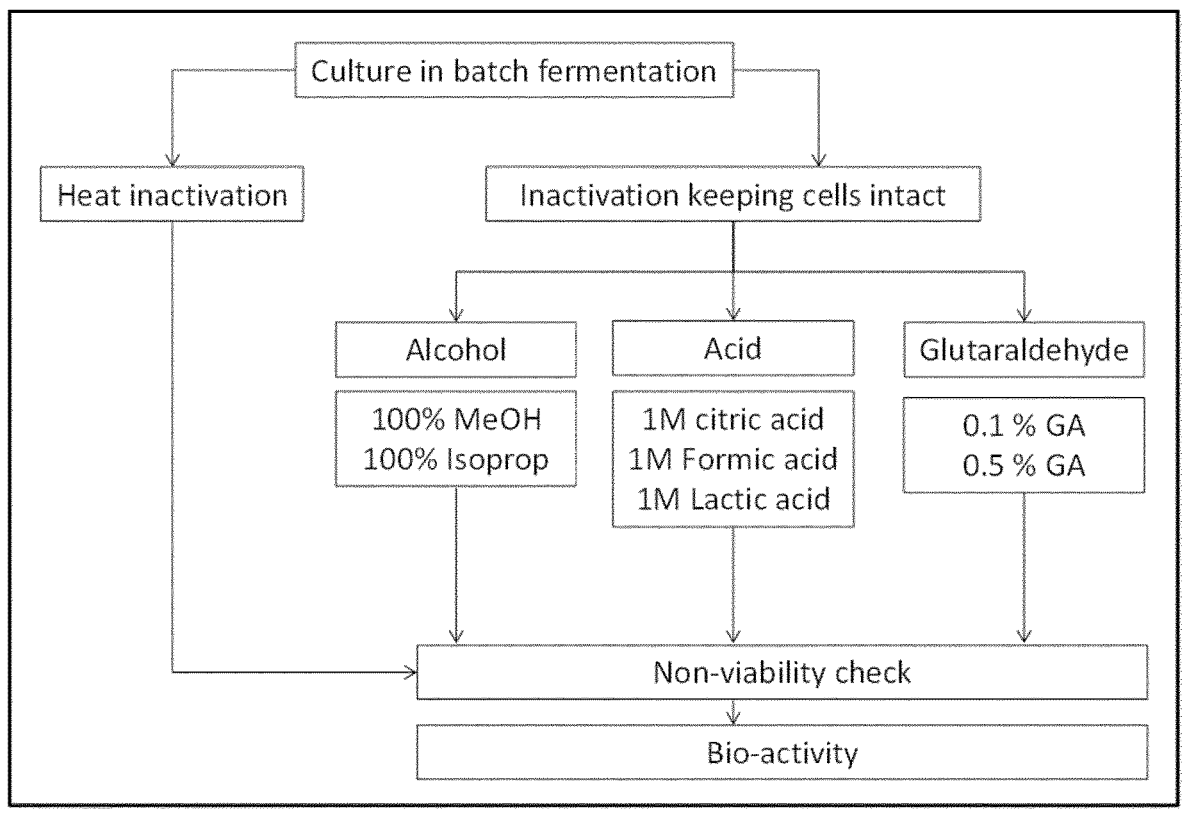

This application is a 371 National Stage application of International Application No. PCT/EP2017/074697, filed Sep. 28, 2017, which claims priority to U.S. Provisional Application No. 62/404,249 filed Oct. 5, 2016, the entire contents of which applications are hereby incorporated by reference.

The present invention relates to control of gene expression by double stranded RNA. In particular the invention relates to a method of enhancing the ability of double stranded RNA administered exogenously—i.e. external to a target organism and under relatively harsh environmental conditions—to silence gene expression in that organism. The invention also relates to compositions for use in the method, and to the use in the method of specific known cross linking agents and/or acids.

The phenomenon of RNA interference potentially to silence gene expression is well known.

RNA is relatively unstable and can be rapidly degraded by, for example, ribonucleases which are ubiquitously present outside of cells. A problem with the application of dsRNA either directly to target organisms, or via exogenous administration to a locus at which they exist concerns the poor stability of the RNA. By exogenous application is meant applied to the target organism in such a way that the organism can incorporate it, or that the dsRNA is produced in a first organism which is different from the target organism and that the target organism incorporates the first organism, or a part thereof comprising the dsRNA so that the said dsRNA is capable of effecting post-transcriptional silencing of a gene comprising a nucleotide sequence corresponding to that comprised by the dsRNA. Exogenous application is distinguished from endogenous production— by which is meant production (generally via expression from an appropriate heterologous sequence) in the cells of the target organism of a double stranded RNA capable of post-transcriptionally silencing targeted genes.

Whilst the exogenously applied dsRNA is generally capable of exerting a relevant biological effect within the short term, perhaps even for up to a few days after application, the effect generally rapidly declines with the dsRNA typically having a half-life of only about 12 to 24 hours in soil for example, and further depending on the precise environmental conditions in which it is administered. Various solutions to this problem have been proposed, including stabilising the dsRNA by encapsulating or otherwise binding it to a polymer which enhances its stability, thus providing for an increased duration of action. There are 2 aspects to the duration of effect. Gene silencing itself will lapse depending on the turnover rate of the relevant protein. In incubation with soil at ambient conditions, dsRNA is degraded within a period of about 2 days. Whilst it is possible for the dsRNA to have an effect substantially longer than this—the advantage of the present invention is to increase the persistence in the environment of the dsRNA.

The present invention is thus concerned with a solution to the problem of relatively rapid inactivation of dsRNA which is applied to an organism exogenously, typically under field conditions which are generally conducive to its rapid degradation or inactivation.

According to the present invention there is provided a method of substantially retaining or otherwise preserving the biological activity of a dsRNA, present in a cell, to post-transcriptionally silence the expression of a gene in a target organism, comprising the step of adding to a composition comprising the cell a compound having the function of a protein—or amine—cross linking agent and/or an acid.

In one aspect of the invention, a polyamine or a protein is added to the cell composition prior to addition of the protein—or amine—cross linking agent, such that the polyamine or protein will bind to carboxylic acid groups on the cell surface and will form an outer stabilizing layer after cross linking, resulting in greater preservation of the biological activity of a dsRNA present in the cell.

The cross linking agent and/or acid may be added to the composition comprising the cell prior to administration of the composition to a locus. By locus is meant a position at which the cell composition comprising the agent is administered, and includes a field in which plants are growing, or in which seeds of cultivated plants are sown, or soil into which will be placed such seeds or plants, or indeed the field, soil, seeds, and/or plants per se.

In a preferred embodiment of the method, the locus is soil, and the composition is applied to it in the vicinity of plants which it is desired to protect by targeting the dsRNA to an essential gene in an insect pest, such as corn rootworm, for example.

The cross linking agent may be selected from the group consisting of polyaldehydes, dialdehydes, di-epoxides, poly epoxides, pyridyl disulfides, carbodiimides, di- or poly-isocyanates, polyfunctional maleimides, di- or poly-imidoesters, bis-diazonium, n-hydroxysuccinimide esters and haloacetals and indeed any other known cross linking agents which comprise at least two functional groups—which may be either the same or different. Some cross-linking agents are sparingly soluble in water, in which case they may conveniently be employed in solutions in suitable solvents, or mixtures of water and such solvents. More preferably, the agent is selected from the group consisting of polyaldehydes and dialdehydes, and still more preferably dialdehydes. The most particularly preferred dialdehyde is glutaraldehyde, specific use of which in the present inventive method is exemplified below. Glutaraldehyde is preferred because its reactivity is such that the reaction is conveniently fast, but not so fast that it is difficult to handle. It is relatively non-toxic, is conveniently water-soluble, readily available and is inexpensive.

The acid may be an organic acid or an inorganic acid. Preferably the acid is a weak acid, more preferably an organic acid, more preferably a 1 to 5 carbon organic acid and most preferably lactic acid or formic acid. Without being limited by any particular interpretation of the mechanism of action, application of acid to inactive cells of the invention may result in the denaturation of proteins resulting in a greater persistence of dsRNA in the environment.

In a particular embodiment, the cells are bacterial cells, although other cells can be used, including algal and even plant or other eukaryotic cells.

In the case that the cells are bacterial cells, the cross linking agent and/or acid may be applied to the cells to inactivate them. Accordingly, the crosslinking agent and acid may have two functions. The first function to inactivate cells and the second to preserve the biological activity of a dsRNA present in the cell.

Alternatively, the cross linking agent and/or acid are provided to cells which have been prior inactivated and have one function—to preserve the biological activity of a dsRNA present in the cell. Various inactivation processes are known in the art, including inactivation by heat (under quite widely varying conditions of temperature and duration), chemical inactivation by the likes of peracetic acid, cupric ascorbate, sodium hypochlorite, hydrogen peroxide, guanidinium thiocyanate, formaldehyde and other mono-aldehydes, and subjecting them to ionizing radiation.

The cross linking agent may be added to the cell composition without an acid, the acid may be added without a cross linking agent, or alternatively both are added to the cell composition—sequentially in any order.

Whatever process is used, the resulting cell composition does not contain any bacteria which are biologically viable.

The cells, which may be prokaryotic, or eukaryotic, are engineered to comprise a DNA sequence which when transcribed yields a double stranded RNA, at least a part of which comprises a sequence which is substantially identical to the sequence of an mRNA of a gene in a prokaryotic or eukaryotic cell, in particular the cell of a plant pest, such as an insect, for example. Typical examples of such insect pests include *Diabrotica virgifera virgifera* (Western corn rootworm), *Diabrotica barberi* (Northern corn rootworm), *Diabrotica undecimpunctata howardi* (Southern corn rootworm), *Diabrotica virgifera zeae* (Mexican corn rootworm) and *Diabrotica speciosa* (cucurbit beetle). Pests against which the dsRNA may be effective also include various pests well known to the agronomist such as nematodes, wireworms and grubs and appropriate soil pathogens such as bacteria and fungi.

The concentration of the cross linking agent present in, or added to, the cell composition is relatively significant. If too much or too little cross linking agent is present, or is added to or is otherwise present at the locus to which the cell composition is added, dsRNA capable of exhibiting a post transcriptional gene silencing effect is not as effective. In the case that the agent is glutaraldehyde, the agent is present in the cell composition/at the locus in an amount of 5 to 0.001%, more preferably 2.5 to 0.005% and most preferably 1 to 0.01%, wherein the % is with respect to the final volume of the cell composition. The skilled artisan will recognize that in order to benefit from both a cell inactivation and dsRNA stabilization effect of the cross linking agent, a higher concentration will be required than when the cross linking agent is added to cells which have been prior inactivated.

Accordingly, when being used to both inactivate cells and stabilize dsRNA, the concentration of crosslinking agent (glutaraldehyde in particular) is at least about 0.1% and preferably the agent is present in the cell composition/at the locus in an amount from 1 to 0.1%. Alternatively, when the cross linking agent is used for dsRNA stabilization and the cells are prior inactivated, the concentration of crosslinking agent (glutaraldehyde in particular) is at least about 0.01% and preferably the agent is present in the cell composition/at the locus in an amount from 1 to 0.01%.

In a preferred embodiment of the method, the cell is a bacterial cell, and the agent is glutaraldehyde which is present in the cell composition in an amount of from 1 to 0.01% by final volume of the composition. Without being limited by any particular interpretation of the mechanism of action, excessive cross-linking agent is understood to reduce bioavailability of dsRNA whereas too little cross-linking agent does not confer the desired improvement in stability and it does not inactivate the cells.

In a preferred embodiment of the method, the cell is a bacterial cell, and the acid is formic acid or lactic acid which is present in the cell composition in an amount of from 1 M to 0.1 M in the composition.

Use of the present inventive method quite significantly extends the duration of the biological activity associated with the dsRNA present in the cell—typically retaining activity in a soil environment at a temperature above about 12 degrees Celsius for periods up to and in excess of 21 days when compared to dsRNA administered to soil but wherein no cross linking agent has been used.

The present invention also includes a composition of matter comprising a cell and a protein cross linking agent, characterised in that the composition comprises soil, the cell comprises dsRNA, and the agent is glutaraldehyde.

The present invention also includes a composition of matter comprising a cell and an acid, characterised in that the composition comprises soil, the cell comprises dsRNA, and the acid is lactic acid or formic acid.

The present invention also includes a cell composition comprising a protein cross linking agent and/or acid added for the purpose of retaining the biological activity of a dsRNA heterologously expressed in the cell as well as the use of a protein cross linking agent and/or acid to substantially stabilize or otherwise preserve the biological activity of a dsRNA present in a cell.

The invention will be further apparent from the following non limiting examples.

EXAMPLES

Generation of Test Samples—Fermentation

A plasmid containing a T7 driven dsRNA expression cassette was transformed into HT115(DE3) *E. coli* cells.

For production of dsRNA, a culture was inoculated from a single colony and was grown overnight in LB medium containing the appropriate antibiotics.

The overnight culture was then diluted to OD600=1 using LB containing the appropriate antibiotics. To induce transcription of the dsRNA, IPTG was added to a final concentration of 1.0 mM. The culture was then incubated for 3.5 hours at 37° C. while shaking at 250 rpm.

After induction, the culture was centrifuged, resuspended at the relevant OD600, typically at 50 to 100 units/ml (where 1 unit corresponds to 1 ml of cells at OD600=1) and the supernatant was discarded. The pellet was then inactivated for further experiments.

Heat inactivation. The bacteria were killed by a heat treatment, typically an HTST treatment, "high-temperature short time" process, which consist of heating the bacterial broth in a flow-through, as is well known for pasteurization methods. The non-viability of the bacteria was confirmed by streaking an aliquot of the treated broth on an LB plate and overnight incubation at 37° C.

Formulation for Increased Soil Stability (FIG. 1).

1) Alcohol treatment: bacterial pellets were resuspended in 100% methanol or 100% isopropanol and stored at 4° C. Prior to setting up the bioassays, samples were dried in a speedvac and resuspended in water, at a relevant OD600.

2) Acid treatment: bacterial pellets were resuspended in 0.5 M final concentration of acid, including citric, formic or lactic acid, pH 3.5. Samples were incubated for 4 hours at room temperature, while shaking at 35 rpm on rollers, thereafter the samples were centrifuged, washed twice with water and resuspended at a relevant OD600. The samples were stored at 4° C. until the bioassay set up.

3) Glutaraldehyde treatment: bacterial pellets were resuspended in 0.1% or 0.5% final concentration of glutaraldehyde. Samples were incubated for 2 hours, 4 hours or 72 hours at room temperature, while shaking at 35 rpm on rollers, then the samples were centrifuged, washed twice and resuspended at a relevant OD600. The samples were stored at 4° C. until the bioassay set up.

For each inactivation method, the non-viability of the bacteria was confirmed by streaking an aliquot of the treated broth on an LB plate and overnight incubation at 37° C.

TEM Microscopy

Figure 2:
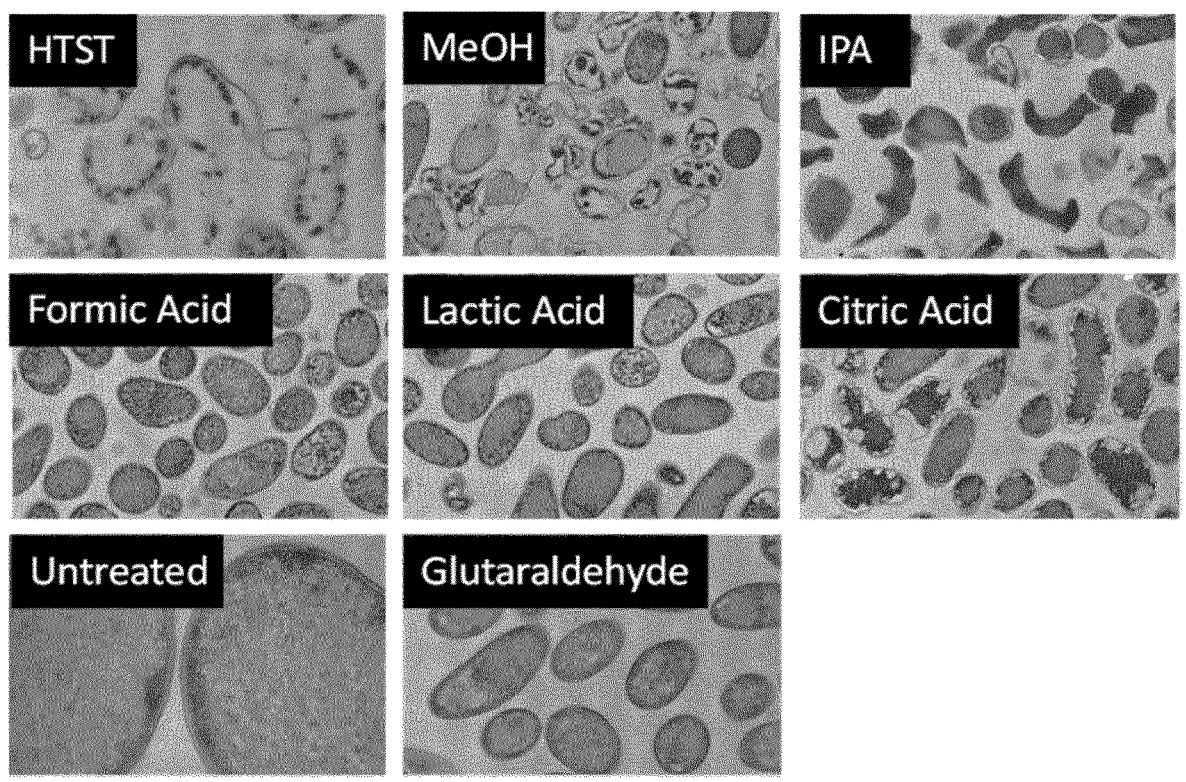
Figure 3:
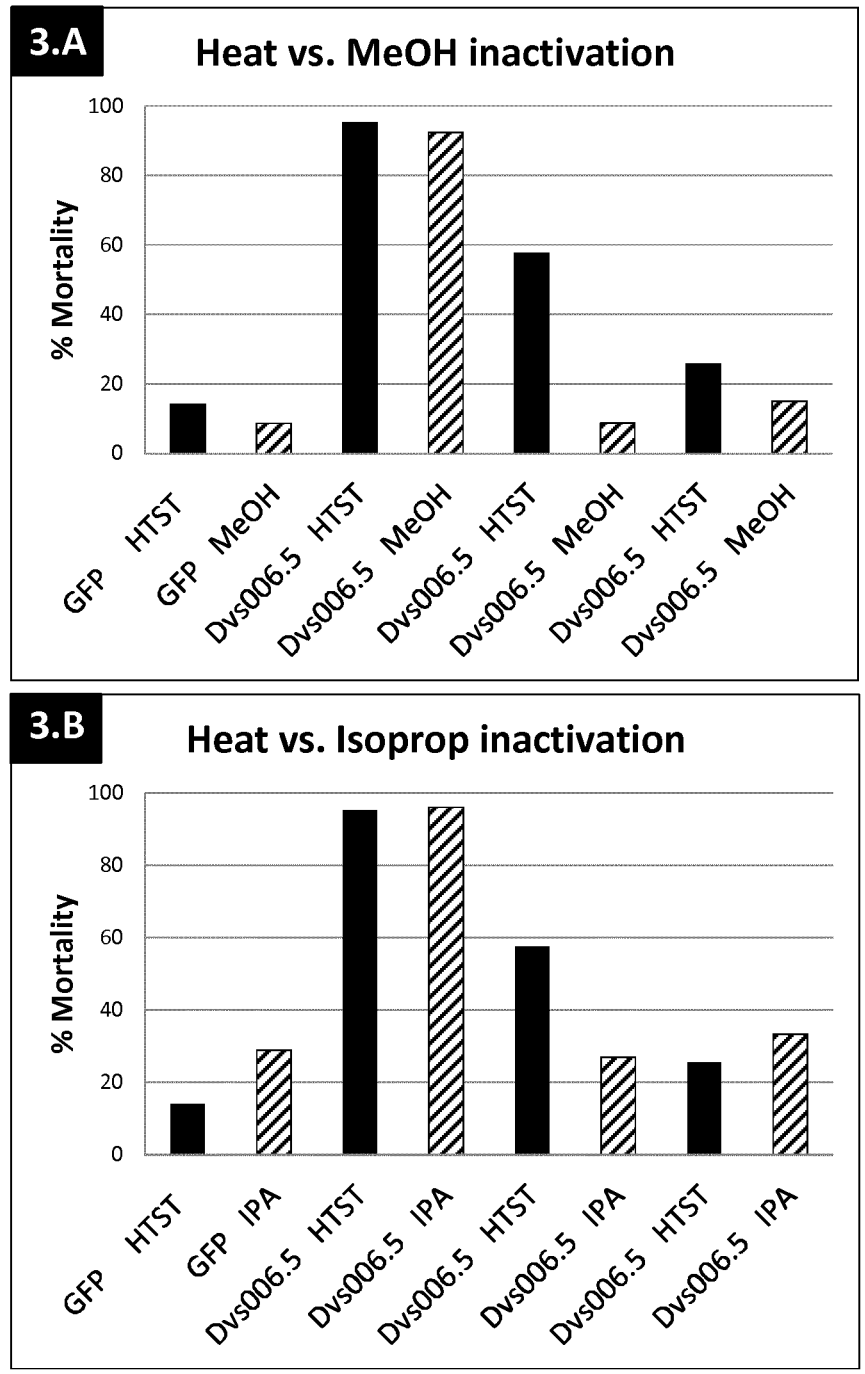
Figure 4:
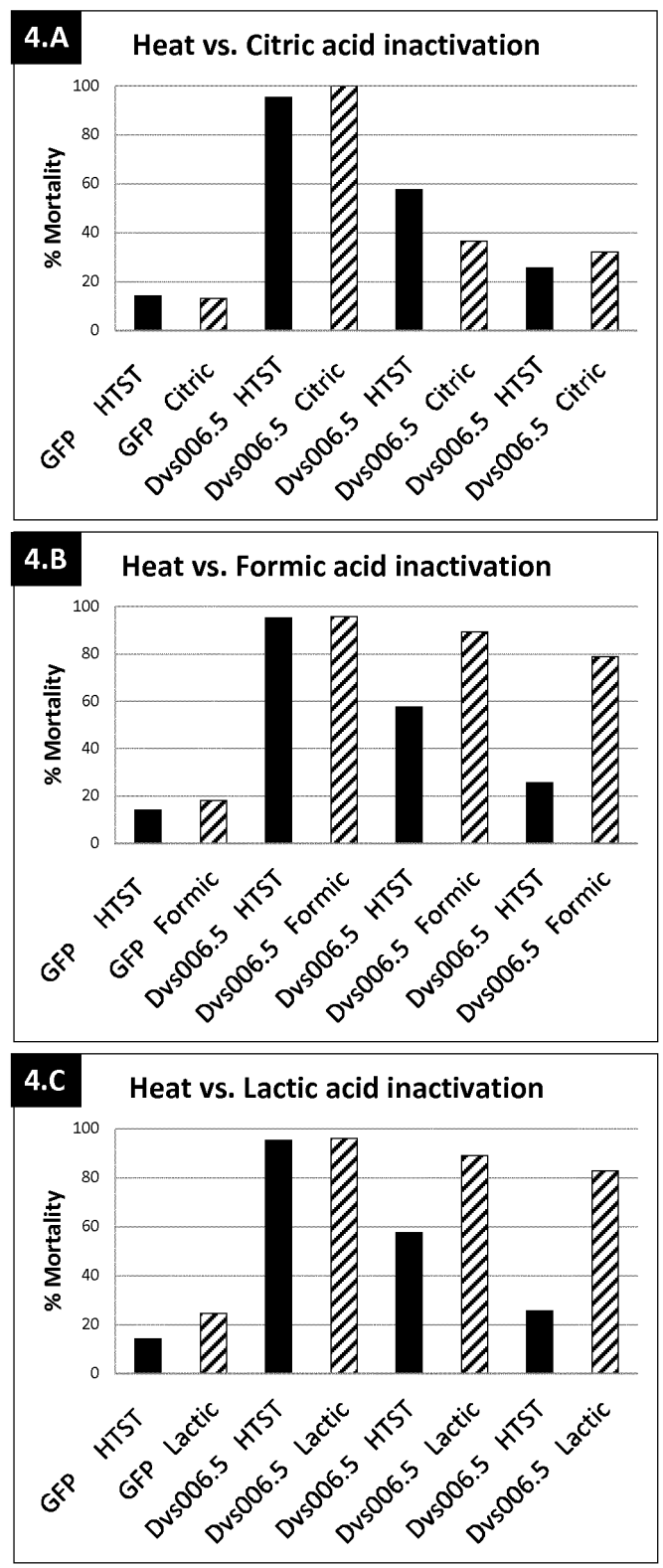
Figure 5:
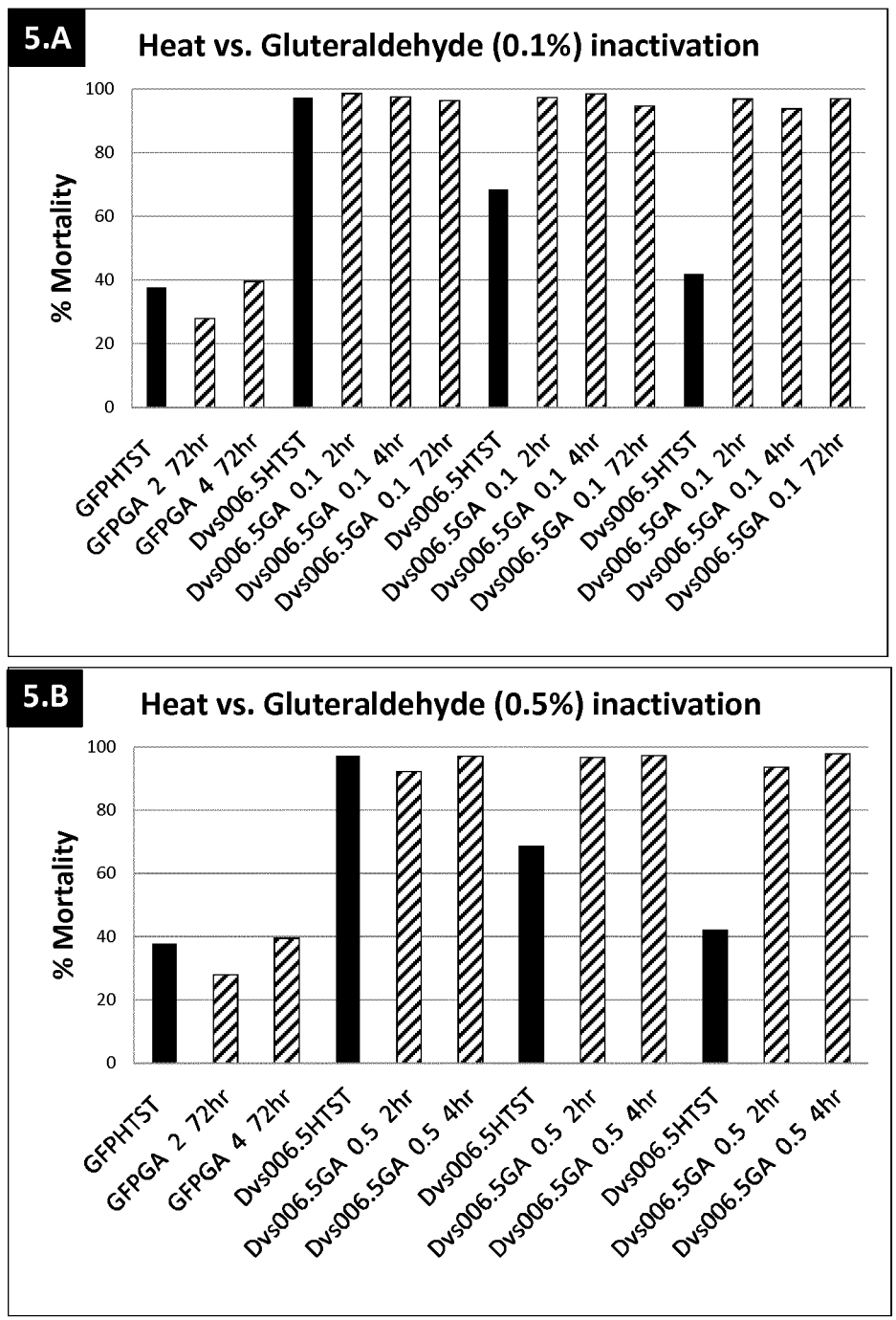

The integrity of the cellular membrane and general aspect of the cells after the inactivation step were checked by TEM microscopy. Briefly, samples were fixed in a sodium cacodylate buffer, containing 2% paraformaldehyde and 2% glutaraldehyde, for 2 hours at room temperature. The samples were then washed and fixed a second time with 1% aqueous OsO4 and rinsed further. After an overnight incubation with a blocking stain solution, 0.5% aqueous uranyl acetate, the samples were washed further, then dehydrated with ethanol and embedded in Spurr resin, followed by a 10 hour incubation in an oven to allow polymerization. The samples were visualized by TEM (FIG. 2).

The results indicated that the cells are intact in the samples inactivated by formic acid, lactic acid and glutaraldehyde, while in the other samples, treated with methanol, isopropanol and citric acid, the cellular structures and the cell wall appeared disrupted.

In soil bio activity assay. An assay was set up using the same samples. Briefly, the different aliquots of active ingredient were prepared by mixing inactivated sample, expressing either the GFP dsRNA control or the active Dvs006.5 dsRNA. The samples tested included the bacterial samples inactivated with heat treatment, glutaraldehyde treatment, acid treatment or alcohol treatment. Different amounts of samples were applied to soil in 48-well plates to reach final concentrations of dsRNA equivalent to 2.5 μg, 25 μg or 50 μg. The plates were incubated at 25° C. for 0, 3 and 7 days, before the infestation to with the larvae.

After 24 hours incubation on the soil plates, at least 30 larvae per treatment were transferred to artificial diet plates (1 larvae per well). The larvae mortality was assessed daily for 7 days. The data for mortality of the larvae at 7 days after infestation is presented (FIGS. 3, 4 and 5). When the active ingredient was added to the soil plates at the day of the larval infestation (Day 0), significant mortality was induced by all the samples, including the inactivation with heat treatment (HTST), alcohol treatments, acid treatments or glutaraldehyde treatments. This indicated that the different inactivation methods were not affecting the bio-availability of the dsRNA.

After 3 or 7 days incubation in the soil, and as expected, a clear decrease in the activity was observed for the HTST samples (<60% mortality at day 3 and <25% mortality at day 7). For the alcohol treatments, methanol and isopropanol respectively, no improvement was observed compared to the HTST control (FIG. 3). Interestingly, for the formic and lactic acid treated samples a clear improvement was observed compared to the HTST control, about 80% mortality was still observed after 3 and day 7 incubation in soil. Citric acid shown not improvement compared to the control (FIG. 4).

For the samples treated with 0.1 or 0.5% glutaraldehyde, the effect was even greater, and the mortality achieved at day 3 and 7 remained above 90%, which was significantly higher than the HTST control (FIG. 5).

The data shows that dsRNA in the bacteria samples treated with 0.5 M formic acid or lactic acid (FIGS. 4.B and C) or glutaraldehyde at the final concentration of 0.1 or 0.5% (FIGS. 5.A and B), were stable in soil for up to 7 days; these treatments provided a method that protects the active ingredient against degradation is the soil, therefore extending the persistence of the dsRNA.

FIGURE LEGENDS

FIG. 1: Representation of the inactivation methods

FIG. 2: TEM microscopy of inactivated cells.

FIG. 3: Comparison of the mortality of the larvae at 7 days after infestation of soil treated with heat inactivated samples (black bars) or with samples treated with (A) methanol or (B) isopropanol (striped bars). In all the samples the target gene corresponded to target Dvs006.5. Samples were applied to soil 0 day, 3 days and 7 days before larval infestation.

FIG. 4: Comparison of the mortality of the larvae at 7 days after infestation of soil treated with heat inactivated samples (black bars) or with samples treated with (A) citric acid, (B) formic acid or (C) lactic acid (striped bars). In all the samples the target gene corresponded to target Dvs006.5. Samples were applied to soil 0 day, 3 days and 7 days before larval infestation.

FIG. 5: Comparison of the mortality of the larvae at 7 days after infestation of soil treated with heat inactivated samples (black bars) or with samples treated with (A) 0.1% glutaraldehyde or (B) 0.5% glutaraldehyde (striped bars). In all the samples the target gene corresponded to target Dvs006.5. Samples were applied to soil 0 day, 3 days and 7 days before larval infestation.

The invention claimed is:

1. A method, comprising:

preparing a composition comprising bacterial cells having a dsRNA present within the cells which post-transcriptionally silences the expression of a gene in a target organism;

adding to the composition glutaraldehyde in a range of 0.01 to 1% with respect to the final volume of the composition to crosslink the bacterial cells; and administering the composition comprising crosslinked bacterial cells to the target organism to control the target organism;

wherein the crosslinked bacterial cells are biologically active and substantially retain or preserve the biological activity of the dsRNA present in a cell at least 3 days longer as compared to only heat treated bacterial cells.

2. A method according to claim 1, wherein the target organism is selected from the group consisting of *Diabrotica virgifera virgifera* (Western com rootworm), *Diabrotica barberi* (Northern com rootworm), *Diabrotica undecimpunctata howardi* (Southern com rootworm), *Diabrotica virgifera zeae* (Mexican com rootworm), *Diabrotica speciosa* (cucurbit beetle), nematodes, wireworms and grubs and appropriate soil pathogens.

3. The method of claim 1, wherein the bacterial cells are substantially inactivated by the glutaraldehyde.

4. The method of claim 3, wherein the bacterial cells have been genetically engineered.

5. The method of claim 4, wherein the target organism is a plant pest.

6. The method of claim 5, wherein the administering occurs by applying the composition to soil.

7. The method of claim 6, wherein the bacterial cells are biologically effective against the plant pest and substantially retain biological effect against the plant pest at least 7 days after application in soil.

8. The method of claim 7, wherein the plant pest is selected from the group consisting of *Diabrotica virgifera virgifera* (Western corn rootworm), *Diabrotica barberi* (Northern corn rootworm), *Diabrotica undecimpunctata howardi* (Southern corn rootworm), *Diabrotica virgifera zeae* (Mexican corn rootworm), *Diabrotica speciosa* (cucurbit beetle), nematodes, wireworms and grubs.

9. The method of claim 8, further comprising washing the composition of cross-linked bacterial cells.

10. The method of claim 8, wherein the glutaraldehyde is at least 0.1%.

11. The method of claim 8, wherein the glutaraldehyde is at least 0.5%.

12. The method of claim 1, wherein the bacterial cells are substantially inactivated prior to the adding of glutaraldehyde.

\* \* \* \* \*